United States Patent [19]
Popovic et al.

[11] Patent Number: 6,008,653
[45] Date of Patent: Dec. 28, 1999

[54] CONTACTLESS SYSTEM FOR DETECTING MICRODEFECTS ON ELECTROSTATOGRAPHIC MEMBERS

[75] Inventors: Zoran D. Popovic, Mississauga; Steven I. Dejak, Sault St. Marie, both of Canada; Satchidanand Mishra, Webster, N.Y.

[73] Assignee: Xerox Corporation, Stamford, Conn.

[21] Appl. No.: 08/960,673

[22] Filed: Oct. 30, 1997

[51] Int. Cl.$^6$ ..................................... G01N 27/60
[52] U.S. Cl. .................. 324/456; 324/457; 324/458
[58] Field of Search .................... 374/456, 457, 374/458

[56] References Cited

U.S. PATENT DOCUMENTS

| | | | |
|---|---|---|---|
| 3,729,675 | 4/1973 | Vosteen | 327/457 |
| 3,898,001 | 8/1975 | Hardenbrook et al. . | |
| 4,134,137 | 1/1979 | Joacobs et al. . | |
| 4,318,042 | 3/1982 | Eda | 324/457 |
| 4,367,948 | 1/1983 | Suzuki | 324/458 |
| 4,683,436 | 7/1987 | Suzuki | 324/458 |
| 5,065,102 | 11/1991 | Takanashi | 324/452 |
| 5,175,503 | 12/1992 | Mishra et al. . | |

OTHER PUBLICATIONS

Z.D Popovic, D. Parco and P. Iglesias, SPIE vol. 1253 Hard Copy and Printing Materials, Media and Processes, 175 (1990).

Zoran Popovic, Pablo Iglesias, "Characterization of Microscopie Elelectrical Non–Uniformities in Xerographic Photoreceptors", Fifth International Congress on Advances and Non–Impact printing Technologies, Nov. 12–17, 1989, San Diego, Calif.

Zoran Popovic, Dave Parco, Pablo Iglesias, "Nature of Microscopic Electrical Defects in organic Photoreceptors", proceedings SPIE–SPSE Electronic Imaging Science and Technology Symposium, Feb. 11–16, 1990, Santa Clara, Calif.

R. Gerhard–Multhaup and W. Perry, J. Phys. E; Sci. Instrum. 16, 421–433 (1983).

E.J. Yarmchuck and G.E. Keefe, J. Appl. Phys 66 (11), Dec. 1, 1989.

*Primary Examiner*—Maura Regan
*Assistant Examiner*—Jose M. Solis

[57] ABSTRACT

A contactless process for detecting surface potential charge patterns in an electrophotographic imaging member including at least one photoconductive imaging layer having an imaging surface, providing a scanner including a capacitive probe having an outer shield electrode, maintaining the probe adjacent to and spaced from the imaging surface to form a parallel plate capacitor with a gas between the probe and the imaging surface, providing a probe amplifier optically coupled to the probe, establishing relative movement between the probe and the imaging surface, maintaining a substantially constant distance between the probe and the imaging surface, applying a constant voltage charge to the imaging surface prior to relative movement of the probe and the imaging surface past each other, synchronously biasing the probe to within about ±300 volts of the average surface potential of the imaging surface, measuring variations in surface potential with the probe, compensating the surface potential variations for variations in distance between the probe and the imaging surface, and comparing the compensated voltage values to a baseline voltage value to detect charge patterns in the electrophotographic imaging member. This process may be conducted with a contactless scanning system comprising a high resolution capacitive probe, a low spatial resolution electrostatic voltmeter coupled to a bias voltage amplifier, and an imaging member having an imaging surface capacitively coupled to and spaced from the probe and the voltmeter, the probe comprising an inner electrode surrounded by and insulated from a coaxial outer Faraday shield electrode, the inner electrode connected to an optocoupled amplifier, and the Faraday shield connected to the bias voltage amplifier.

27 Claims, 16 Drawing Sheets

FIG. 6
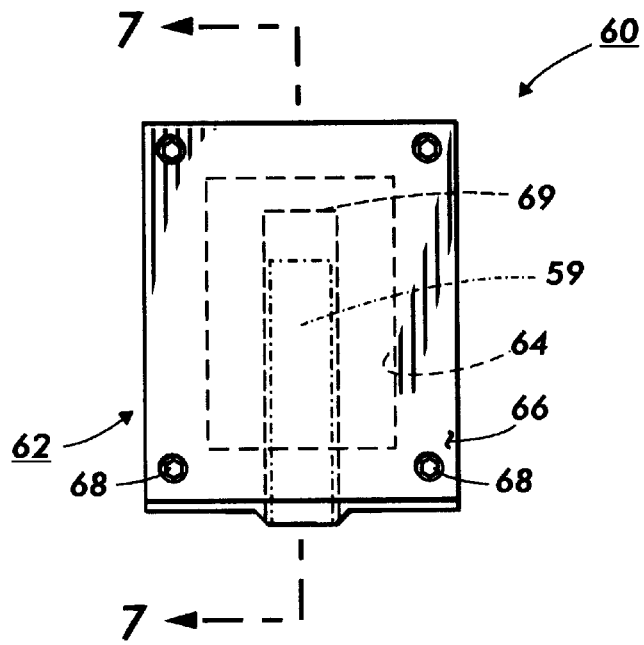
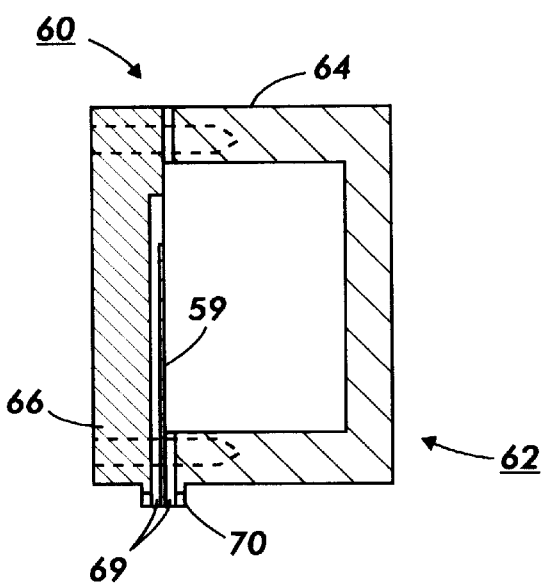
FIG. 7

CONTACTLESS SYSTEM FOR DETECTING MICRODEFECTS ON ELECTROSTATOGRAPHIC MEMBERS

BACKGROUND OF THE INVENTION

This invention relates in general to electrostatography and, more specifically, to apparatus and process for detecting microdefects in xerographic photoreceptors with a contactless system.

Electrostatography is well known and includes, for example electrography and electrophotography. In electrography, an electrostatic latent image is formed on a nonelectrophotographic imaging member by various means such as styli, shaped electrodes, ion streams and the like. This electrostatic latent image may then be developed to form a visible image by depositing finely divided electroscopic marking particles on the imaging surface.

In the art of xerography, a xerographic plate or photoreceptor comprising a photoconductive insulating layer is imaged by first uniformly depositing an electrostatic charge on the imaging surface of the xerographic plate and then exposing the plate to a pattern of activating electromagnetic radiation such as light which selectively dissipates the charge in the illuminated areas of the plate while leaving behind an electrostatic latent image in the non-illuminated areas. This electrostatic latent image may then be developed to form a visible image by depositing finely divided electroscopic marking particles on the imaging surface.

A photoconductive layer for use in xerography may be a homogeneous layer of a single material such as vitreous selenium or it may be a composite layer containing a photoconductor and another material. One type of composite photoconductive layer used in electrophotography is illustrated in U.S. Pat. No. 4,265,990, the entire disclosure thereof being incorporated herein by reference. A photosensitive member is described in this patent having at least two electrically operative layers. One layer comprises a photoconductive layer which is capable of photogenerating holes and injecting the photogenerated holes into a contiguous charge transport layer. Generally, where the two electrically operative layers are positioned on an electrically conductive layer with the photoconductive layer sandwiched between a contiguous charge transport layer and the conductive layer, the outer surface of the charge transport layer is normally charged with a uniform electrostatic charge and the conductive layer is utilized as an electrode. In flexible electrophotographic imaging members, the electrode is normally a thin conductive coating supported on a thermoplastic resin web. Obviously, the conductive layer may also function as an electrode when the charge transport layer is sandwiched between the conductive layer and a photoconductive layer which is capable of photogenerating electrons and injecting the photogenerated electrons into the charge transport layer. The charge transport layer in this embodiment, of course, must be capable of supporting the injection of photogenerated electrons from the photoconductive layer and transporting the electrons through the charge transport layer.

The photoreceptors are usually multilayered and comprise a substrate, an optional conductive layer (if the substrate is not itself conductive), an optional hole blocking layer, an optional adhesive layer, a charge generating layer, and a charge transport layer and, in some belt embodiments, an anti-curl backing layer.

Although excellent toner images may be obtained with multilayered photoreceptors, it has been found that as more advanced, higher speed electrophotographic copiers, duplicators and printers were developed, reduced life would occasionally be encountered during extended cycling. Surprisingly, cycling of photoreceptors made up of identical materials but differing in overall size and use in different copiers, duplicators and printers exhibited different life spans where one of the causes of failure was dark decay. Moreover, photoreceptors from different production runs had different life spans when cycled to the point of dark decay failure in any given copier, duplicator and printer. Since photoreceptor properties can vary from one production run to another and also during cycling, copy quality in many machines is maintained by feedback control system which constantly adjusts the machine operating parameters to compensate for the variations in the dark decay electrical characteristic of any given photoreceptor. Thus, photoreceptor life is partially governed by the design of the control system and this leads to different life spans in different machines for the same photoreceptor where failure is due to unacceptable dark decay. However, even the control system of any given machine cannot compensate for variations in photoreceptor dark decay characteristics that extend outside the operating range of the control system.

In the production of electrophotographic imaging members the complex nature of the manufacturing process renders unpredictable electrical characteristics of the coated photoreceptor from batch to batch and from month to month. For example, reduction of photoreceptor life due to changes in environment affects the installation or adjustment of new coating applicators or the initial use of a newly prepared batch of coating material for one of the many layers of the photoreceptors such as the hole blocking layer, charge generating layer, or charge transport layer are difficult to identify within a reasonable length of time subsequent to the point in time that the photoreceptor comes off the production line.

In a photoreceptor, many types of microdefects can be a source of xerographic image degradation. These microdefects can be occlusions of particles, bubbles in the coating layers, microscopic areas in a photoreceptor without charge generator layer, coating thickness nonuniformities, dark decay nonuniformities, light sensitivity nonuniformities, and charge deficient spots (CDS's). This last type of defect, charge defficient spots, or CDS's are localized areas of discharge without activation by light. They can cause two types of image defects, depending on the development method utilized. Charge deficient spots usually can be detected only electrically or by xerographic development and so far have eluded microscopic or chemical detection.

In discharged area development, the photoreceptor is negatively charged. An electrostatic latent image, as a charge distribution, is formed on the photoreceptor by selectively discharging certain areas. Toner attracted to discharged areas develops this latent image. Laser printers usually work on this principle. When charge deficient spots are present on the photoreceptor, examination of the final image after toner transfer form the photoreceptor to a receiving member such as paper reveals dark spots on a white background due to the absence of negative charge in the charge deficient spots.

In charged area development, usually used in light lens xerography, the toner image is formed by developing the charged areas on a photoreceptor. After transfer of the toner image to a receiving member such as paper, the charge deficient spot on the photoreceptor will result in a small white spot in a black background called a microwhite, which is not as noticeable as a "microblack" spot, characteristic of discharged area development.

One technique for detecting charge deficient spots in photoreceptors from a specific production run is to actually cycle the photoreceptor in the specific type of copier, duplicator and printer machine for which the photoreceptor was fabricated. Generally, it has been found that actual machine testing provides the most accurate way of detecting charge deficient spots in a photoreceptor from a given batch. However, machine testing for detecting charge deficient spots is a very laborious and time consuming process which requires involving hand feeding of sheets by test personnel along with constant monitoring of the final quality of every sheet. Moreover, accuracy of the test results depends a great deal upon interpretations and behavior of the personnel that are feeding and evaluating the sheets. Further, since machine characteristics vary from machine to machine for any given model or type, reliability of the final test results for any given machine model must factor in any peculiar quirks of that specific machine versus the characteristics of other machines of the same model or type. Because of machine complexity and variations from machine to machine, the data from a test in a single machine is not sufficiently credible to justify the scrapping of an entire production batch of photoreceptor material. Thus, tests are normally conducted in three or more machines. Since a given photoreceptor may be used in different kinds of machines such as copiers, duplicator and printers under markedly different operating conditions, the charge deficient spots detection based on the machine tests of a representative test photoreceptor sample is specific to the actual machine in which photoreceptors from the tested batch will eventually be utilized. Thus, photoreceptor tests on one machine will not necessarily predict whether the appearance of charge deficient spots will occur if the same type of photoreceptor were used in another different type of machine. Thus, for a machine charge deficient spot test, the test would have to be conducted on each different type of machine. This becomes extremely expensive and time consuming. Moreover, because of the length of time required for machine testing, the inventory of stockpiled photoreceptors waiting approval based on life testing of machines can reach unacceptably high levels. For example, a batch may consist of many rolls, with each roll yielding thousands of belts. Still further delays are experienced subsequent to satisfactory charge deficient spot testing because the webs must thereafter be formed into belts, packaged and shipped.

Another test method utilizes a stylus scanner such as that described by Z. D. Popovic et al., "Characterization of microscopic Electrical Defects in Xerographic Photoreceptors", *Journal of Imaging Technology*, vol. 17, No. 2, April/May, 1991, pp. 71–75. The stylus scanner applies a bias voltage to a shielded probe, which is immersed in silicone oil and is in contact with the photoreceptor surface. The silicone oil prevents electrical arcing and breakdown. Current flowing through the probe contains information about defects, and scanning speeds up to 6×6 mm$^2$ in about 15 minutes were achieved. Although the stylus scanner is a highly reproducible tool which enabled some important discoveries about the nature of charge deficient spots, it has the basic shortcoming of low speed.

Many attempts have also been made in the past to reduce the time of scan by designing contactless probes. For example, a probe has been described in the literature and used for readout of xeroradiographic (X-ray) amorphous selenium plates, e.g. W. Hillen, St. Rupp, U. Schieble, T. Zaengel, Proc. SPIE, Vol. 1090, Medical Imaging III, Image Formation, 296 (1989); W. Hillen, U. Schieble, T. Zaengel;. Proc. SPIE, Vol. 914, Medical Imaging II, 253 (1988); U. Schieble, W. Hillen, T. Zaengel;. Proc. SPIE, Vol. 914, Medical Imaging II, 253 (1988); U. Schieble, T. Zaemge;. Proc. SPIE, Vol. 626, Medicine XIV/PACS IV, 86 (1986); These probes rely on reducing the distance of a probe to a photoreceptor surface in order to increase resolution of the measurements. The typical distance of the probe to the photoreceptor surface is 50–150 micrometers. In order to avoid air breakdown the ground plane of a xeroradiographic plate is biased appropriately to provide approximately zero voltage difference between the probe and photoreceptor surface.

Thus, there is a need for higher scanning speeds without arcing for applications such as electrostatographic member production monitoring.

INFORMATION DISCLOSURE STATEMENT

U.S. Pat. No. 5,175,503 to Mishra et al., issued Dec. 29, 1992—A process for ascertaining the projected imaging cycle life of an electrophotographic imaging member is disclosed including the steps of (a) providing at least one electrophotographic imaging member having a cycling life of a known number of imaging cycles, the imaging member comprising an electrically conductive layer and at least one photoconductive layer, (b) repeatedly subjecting the electrophotographic imaging member to cycles comprising electrostatic charging and light discharging steps, (c) measuring dark decay of the photoconductive layer during cycling until the amount of dark decay reaches a crest value, (d) establishing with the crest value a reference datum for dark decay crest value versus imaging cycles, (e) repeatedly subjecting a virgin electrophotographic imaging member to aforesaid cycles comprising electrostatic charging and light discharging steps until the amount of dark decay reaches a crest value which remains substantially constant during further cycling, and (f) comparing the dark decay crest value of the virgin electrophotographic imaging member with the reference datum to ascertain the projected cycling life of the virgin electrophotographic imaging member.

Z. D. Popovic, D. Parco and P. Iglesias, SPIE Vol. 1253 Hard Copy and Printing Materials, Media and Processes, 175 (1990)—A scanning stylus instrument is described for use in the investigation of the electrical properties of individual microscopic defects in organic photoreceptors. A schematic diagram of the measurement circuitry is shown in FIG. 1 on page 176.

Zoran Popovic, Pablo Iglesias, "Characterization of Microscopic Electrical Non-Uniformities in Xerographic Photoreceptors", Fifth International Congress on Advances and Non-Impact Printing Technologies, Nov. 12–17, 1989, San Diego, Calif.—An approach to study electrical nonuniformities in photoreceptors is disclosed in which a shielded stylus is used to scan a photoreceptor while in intimate contact with the photoreceptor surface. The photoreceptor is carried on a computer controller X-Y stage. The ground plane of the photoreceptor is connected to the high voltage power supply through a resistor and high voltage relay. A polished stylus tip is brought into contact with the photoreceptor surface. The stylus tip is immersed in silicon oil to prevent electrical breakdown. The presence of silicon oil insulation is absolutely necessary for reproducible measurements. The stylus shield is grounded and the sensing electrode connected to an electrometer to measure the charge flow as voltage is applied to the sample. The whole system is controlled as Xerox 6065 personal computer.

Zoran Popovic, Dave Parco, Pablo Iglesias, "Nature of Microscopic Electrical Defects in Organic Photoreceptors", Proceedings SPIE-SPSE Electronic Imaging Science and Technology Symposium, Feb. 11–16, 1990, Santa Clara, Calif.—The device described in the paper entitled "Characterization of Microscopic Electrical Non-Uniformities in Xerographic Photoreceptors", above, is used to investigate the electrical properties of individual microscopic electrical defects in organic xerographic photoreceptors. The shape of individual microscopic electrical defects were mapped and their current-voltage characteristics were measured.

R. Gerhard-Multhaupt and W. Perry, J. Phys. E; Sci. Instrum. 16, 421–422 (1983).—A scanning capacitive probe is described for the measurement of surface-charge distributions on an electret foils. The probe is a MOSSET electrometer follower together with a high resolution adapter.

E. J. Yarmchuck and G. E. Keefe, J. Appl. Phys. 66 (11), Dec. 1, 1989.—A technique is disclosed for direct, quantitative measurements of surface charge distributions on photoconductors. The photoconductors are carried on a stepping table from a corona charging station to an exposure station and then to the measurement station. Surface charge distribution is determined by a sequence of point-by-point charge measurements at different locations relative to the exposure. Charge measurements are made with an electrometer.

U.S. Pat. No. 3,898,001 to Hardenbrook et al, issued Aug. 5, 1975.—An electrometer system is disclosed which measures electrostatic charges such as a charge level on a photoconductor surface. The electrometer measures a drop in surface voltage in an absence of light on a photoreceptor which is characterized as dark decay, e.g. see Column 1, lines 27–52. The electrometer can measure the remaining or background voltage on a photoreceptor remaining after exposure. The control of this background voltage is important for proper development and copy quality.

U.S. Pat. No. 4,134,137 to Jacobs et al, issued Jan. 9, 1979—A single wire microelectrometer imaging system is disclosed which includes a means to measure dark decay. A photoreceptor can be selected to minimize dark decay due to a scanning process requiring a finite length of time. A multiple probe electrometer array is provided which comprises a number of single probe electrometers which increase the electronics and gap maintenance complexity while reducing mechanics, image interlace complexities, and processing time.

CROSS REFERENCE TO COPENDING APPLICATIONS

Copending patent application Ser. No. 08/585,133, filed in the name of S. Mishra on Jan. 11, 1996—A process is disclosed for ascertaining the microdefect levels of an electrophotographic imaging member comprising the steps of measuring either the differential increase in charge over and above the capacitive value or measuring reduction in voltage below the capacitive value of a known imaging member and of a virgin imaging member and comparing differential increase in charge over and above the capacitive value or the reduction in voltage below the capacitive value of the known imaging member and of the virgin imaging member.

Copending patent application Ser. No. 08/961,061, (Docket No. D/96637Q), entitled CONTACTLESS SYSTEM FOR DETECTING SURFACE POTENTIAL CHARGE PATTERNS, filed in the names of S. Mishra et al. concurrently herewith—A contactless process is disclosed for detecting surface potential charge patterns in an electrostatographic imaging member comprising providing a cylindrical electrostatographic imaging member having an outer imaging surface and an imaginary axis, providing an electrostatic voltmeter probe, maintaining the distance of the electrostatic voltmeter probe to the imaging surface substantially constant, the distance between the voltmeter probe and the imaging member being slightly greater than the minimum distance at which Paschen breakdown will occur, maintaining the probe adjacent to and spaced from the imaging surface to form a parallel plate capacitor with a gas between the probe and the imaging surface, establishing relative movement between the probe and the imaging surface, maintaining a substantially constant distance between the probe and the imaging surface, depositing a charge to the imaging surface immediately prior to relative movement of the probe over the imaging surface, the deposited charge having a surface potential, and measuring low resolution variations in the surface potential over a distance of between about 0.1 millimeter and about 5 millimeters with the probe. Preferably, the charge is deposited only along a predetermined narrow path having a width of between about 0.5 millimeter and about 20 millimeters. A contactless scanning system for carrying out the process is also disclosed.

Copending patent application Ser. No. 08/961,436, (Docket No. D/97236), entitled CONSTANT DISTANCE SCANNER PROBE SYSTEM, filed in the names of Z. Popovic et al. concurrently herewith—A contactless system is disclosed comprising a movable device spaced from an outer surface of a member, the movable device comprising at least one passageway for directing at least one stream of a gas from the moveable device toward the outer surface of the member with sufficient force to maintain the movable device a constant distance from the outer surface of the member. This system may be utilized in a process comprising providing a movable device spaced from an outer surface of a member, the movable device comprising at least one passageway for directing at least one stream of a gas from the moveable device toward the outer surface of the member, passing gas through the passageway with sufficient force to maintain the movable device a constant distance from the outer surface of the member.

BRIEF SUMMARY OF THE INVENTION

It is, therefore, an object of the present invention to provide improved processes and apparatus for detecting charge deficient spots an electrostatographic imaging member which overcomes the above-noted deficiencies.

It is still another object of the present invention to provide improved processes and apparatus for more accurately assessing charge deficient spots for in electrostatographic imaging members.

It is another object of the present invention to provide improved processes and apparatus for more accurately assessing charge deficient spots in electrostatographic to be employed in discharged area development systems.

It is yet another object of the present invention to provide improved processes and apparatus for determining charge deficient spots in electrostatographic imaging members to be employed in charged area development systems.

It is another object of the present invention to provide improved processes and apparatus for assessing charge deficient spots in electrostatographic imaging members without contacting the imaging surface of the imaging member.

The foregoing objects and others are accomplished in accordance with this invention by providing a contactless process for detecting surface potential charge patterns in an electrophotographic imaging member comprising at least one photoconductive imaging layer having a first major surface on one side and a second major surface on the opposite side, the second major surface comprising an imaging surface, providing a scanner comprising a capacitive probe having an outer shield electrode, maintaining the probe adjacent to and spaced from the imaging surface to form a parallel plate capacitor with a gas between the probe and the imaging surface, providing a probe amplifier optically coupled to the probe, establishing relative movement between the probe and the imaging surface, maintaining a substantially constant distance between the probe and the imaging surface, applying a constant voltage charge to the imaging surface prior to relative movement of the probe and the imaging surface past each other, synchronously biasing the probe to the average surface potential of the imaging surface, measuring variations in surface potential with the probe, compensating the surface potential variations for variations in distance between the probe and the imaging surface, and comparing the compensated voltage values to a baseline voltage value to detect charge patterns in the electrophotographic imaging member. This process may be conducted with a non-contact scanning system comprising a high resolution capacitive probe, a low spatial resolution electrostatic voltmeter coupled to a bias voltage amplifier, and an imaging member having an imaging surface capacitively coupled to and spaced from the probe and the voltmeter, the probe comprising an inner electrode surrounded by and insulated from a coaxial outer Faraday shield electrode, the inner electrode connected to an opto-coupled amplifier, and the Faraday shield connected to bias voltage amplifier.

BRIEF DESCRIPTION OF THE DRAWINGS

A more complete understanding of the present invention can be obtained by reference to the accompanying drawings wherein:

FIGS. 6 and 7 are front and side views of a rectangular scanner probe embodiment for the optically coupled scanner system of this invention.

These figures merely schematically illustrate the invention and are not intended to indicate relative size and dimensions of the device or components thereof.

DETAILED DESCRIPTION OF THE DRAWINGS

Figure 1:
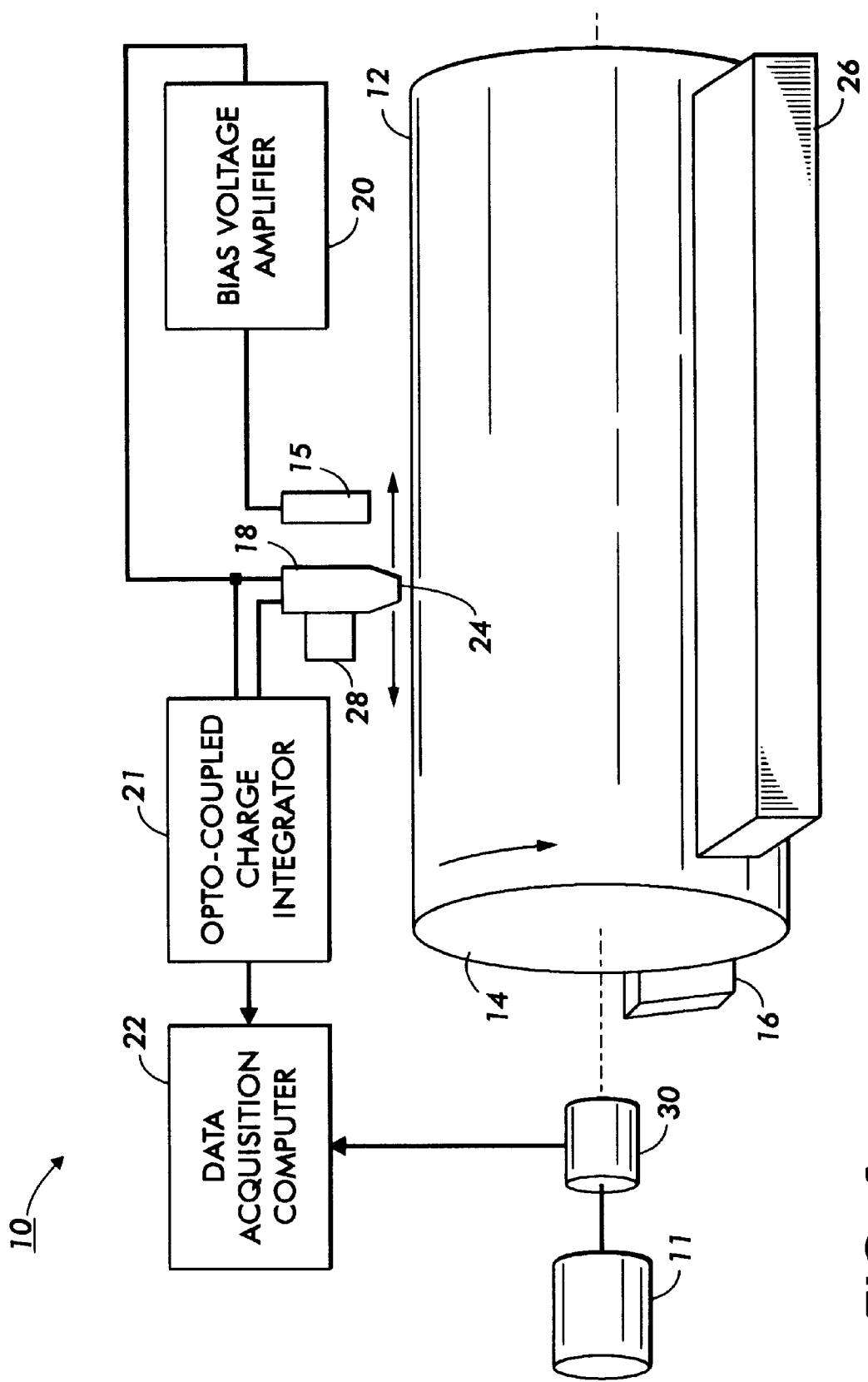
FIG. 1 is a schematic illustration of an embodiment of an optically coupled scanner system of this invention.

Referring to FIG. 1, a schematic of a scanner system 10 of this invention is shown. Drum is rotated at constant speed by a stepper motor 11. Similar to a xerographic imaging system, a flexible photoreceptor belt 12 mounted on an electrically conductive grounded rotatable drum 14 is charged with a scorotron 16, which electrostatically charges the photoreceptor belt 12 to a constant voltage. Alternatively, the drum 14 may be a photoreceptor drum substrate coated with at least one electrophotographic coating 12. A low resolution electrostatic voltmeter probe 15 and bias voltage amplifier 20 maintain approximately a zero voltage difference between a high resolution probe 18 and average surface potential of photoreceptor belt 12. The high resolution probe 18, opto-coupled charge integrator 21 and data acquisition computer 22 measure changes in the potential of the moving photoreceptor belt 12 after charging. The lower end 24 of probe 18 has a smooth surface which is parallel to and typically positioned about 100 $\mu$m above the outer imaging surface of belt 12. Time consumed for a section of photoreceptor belt 12 just charged by scorotron 16 to reach probe 18 allows charge deficient spots to form before the spots are scanned by probe 18. Charge on belt 12 is removed with erase light 26 after photoreceptor belt 12 passes probe 18. A stepper motor and micrometer screw combination 28 moves the probe 18 to a new scan line position and the process is repeated. Measurements are started for each scan line by a pulse from encoder 30 at a constant angular position. The "direction of scan" or "scanning direction", as employed herein is defined as the direction of relative movement of the probe over the imaging surface of the photoreceptor belt or drum during the period when probe readings are taken, e.g., in the embodiment shown in FIG. 1, the "scanning direction" would be along a circular path around the circumference of the drum because the drum is rotating past a stationary probe during data acquisition.

The combination of the lower end 24 of probe 18 and the outer imaging surface of photoreceptor belt 12 form a small parallel plate capacitor. It is through this capacitance that a charge deficient spot is detected. Without insulation, the center electrode 32 (see FIG. 2) of probe 18 has a circular cross section with a typical diameter of 113 $\mu$m. At a typical distance of 100 $\mu$m between probe end 24 (which includes the end of center electrode 32) and the outer imaging surface of photoreceptor belt 12, the capacitance is found to be approximately 1 fF, using the approximate relation $$C = \frac{A\varepsilon_o}{d}.$$

The voltage across this capacitance will be 100 V if 0.1 pC (Q=CV) of charge is present on the probe end 24. Since the capacitance is inversely proportional to distance, as the gap between probe end 24 and photoreceptor 12 decreases, the variation of capacitance with change in distance increases. Mathematically, if $$C = \frac{A\varepsilon_0}{d} \text{ then } \Delta C = \frac{-A\varepsilon_o}{d^2}\Delta d,$$

which is larger for small distances. Precise machining of the scanner mechanical hardware prevents excessive measurement errors from gap distance variations. Vibrations from the stepper motor 11 are reduced by selecting a smooth running micro-stepping motor. Stepper motor and micrometer screw combination 28 used for incremental probe motion parallel to the drum axis does not contribute to noise, since it is not operated at the time data is acquired by probe.

Figure 2:
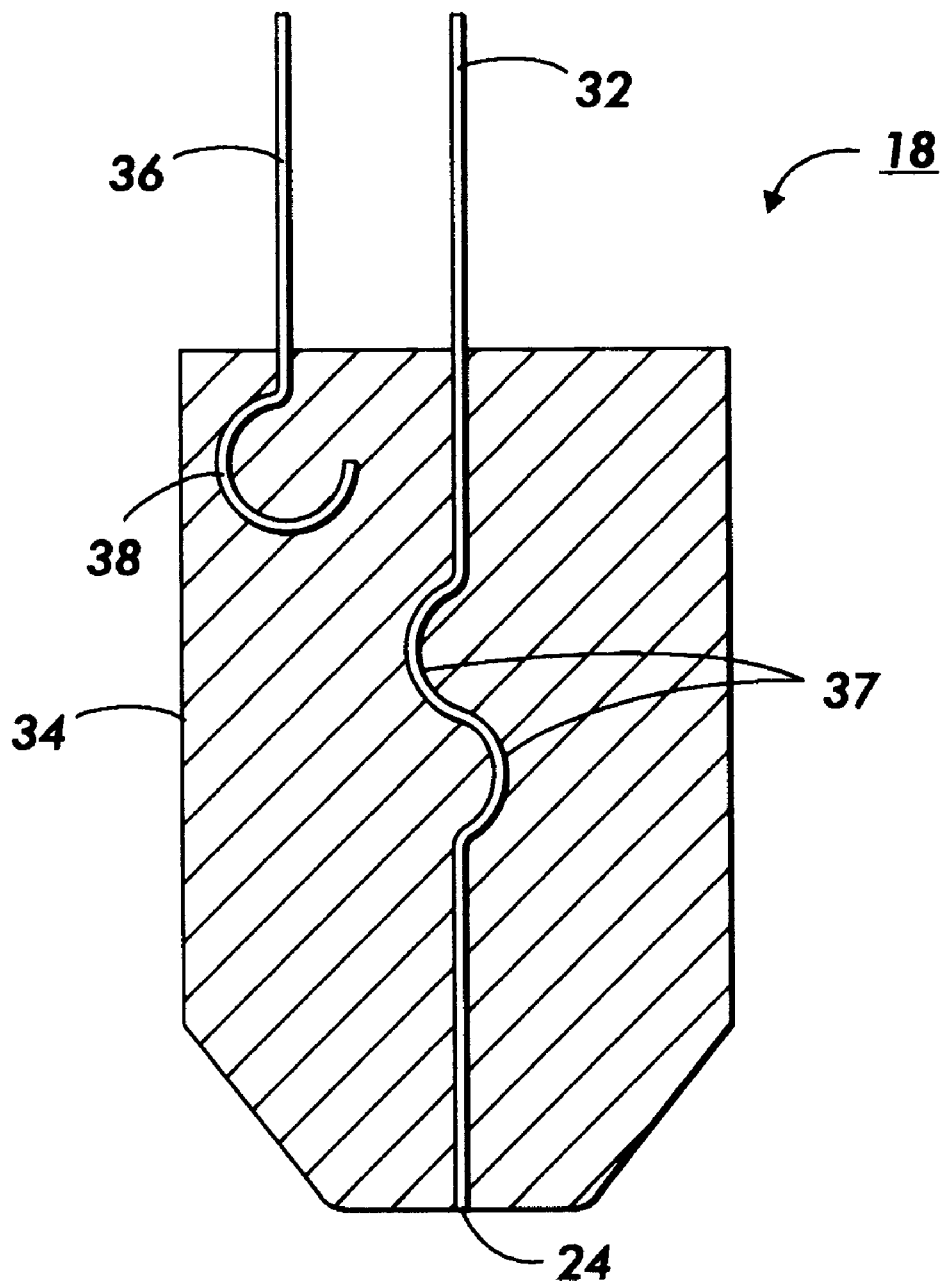
FIG. 2 is a schematic sectional side view in elevation of a circular scanner probe employed in the optically coupled scanner system of this invention.

As shown in FIG. 2, probe 18 is well shielded from external noise and rendered suitably rugged by embedding a small diameter wire center electrode 32 in a shield electrode 34 which is electrically grounded via ground wire 36. The small diameter wire center electrode 32 is enameled, i.e. coated with a thin electrically insulating coating (not shown). Any suitable insulating coating may be utilized. Generally, the insulating coating is a film forming material having a resistivity in excess of about $10^{13}$ ohm cm and a thickness between about 5 micrometers and about 50 micrometers. Grounded shield electrode 34 is used as a shield against electromagnetic noise. Changes in potential are sensed by the embedded center electrode 32. Any suitable technique may be utilized to fabricate probe 18. One technique involves the use of a small plastic cylindrical container having a conical tip such as containers used for preparation of samples for electron microscopy. This container is used as a mold. A small hole punched into the tip of the container allows an enameled wire to be threaded through to form center electrode 32. A series of small bends 37 in the wire for center electrode 32 and the surrounding of the wire with shield electrode 34 prevents a tendency of the wire to recess into the shield, and in some cases, pull out of the shield entirely. The capacitive coupling between the end 24 of probe 18 and the outer imaging surface of photoreceptor 12 will change as the center electrode 32 begins to recess into the shield thus adversely affecting readings. With the enameled wire for center electrode 32 centered in the mold, heat can be applied by any suitable source such as a hot plate. Low melting temperature metal such as an alloy of bismuth, tin, lead and cadmium having a melting temperature of 70° C. may be used for the shield electrode 34 of probe 18. A soldering iron or other suitable heat source may be used to melt the metal before it is poured into the mold. To provide an electrical ground connection to the shield electrode 34 a bare ground wire 36 with a loop 38 at its embedded end is also placed into the molten metal. Once cooled, the probe 18 is carefully removed from the mold. Probe 18 may be polished by any suitable technique such as mounting the probe in a double cantilever polishing structure. Using emery cloth and diamond paste, the tip can be polished to a high finish with no defects in the shield electrode 34. The edges of probe 18 may be slightly rounded to remove any sharp edges. The preferred double cantilever polishing ensures that the polished surface lower end 24 of probe 18 is perpendicular to the centerline of probe 18. Excessive electric fields are thus prevented and, if probe 18 happens to come into contact with photoreceptor 12, scratches will be minimized. Also by polishing, the lower end of center electrode 32 and bottom of shield electrode 34 are at the same plane to achieve good shielding and detection properties. If center electrode 32 is recessed too far into shield electrode 34, more electric flux will go into the shield electrode 34 rather than onto the center electrode 32 thereby reducing the signal. If the lower end of center electrode 32 extends beyond shield electrode 34, it could scratch photoreceptor 12. Thus, it is preferred that the lower end of center electrode 32 and the lower end of shield electrode 34 be substantially flush with each other.

As described above, a typical gap distance of 100 μm between the lower end 24 of probe 18 and a voltage of 100 volts corresponds to 0.1 pC of charge induced into probe 18. Preferably, the gap distance is between about 20 micrometers and about 200 micrometers and more preferably between about 50 micrometers and about 100 micrometers. When the gap is less than about 20 micrometers, there is increased risk of probe touching the surface which can lead to erroneous results. If the gap is greater than about 200 micrometers, the probe sensitivity and resolution are substantially reduced.

Figure 3:
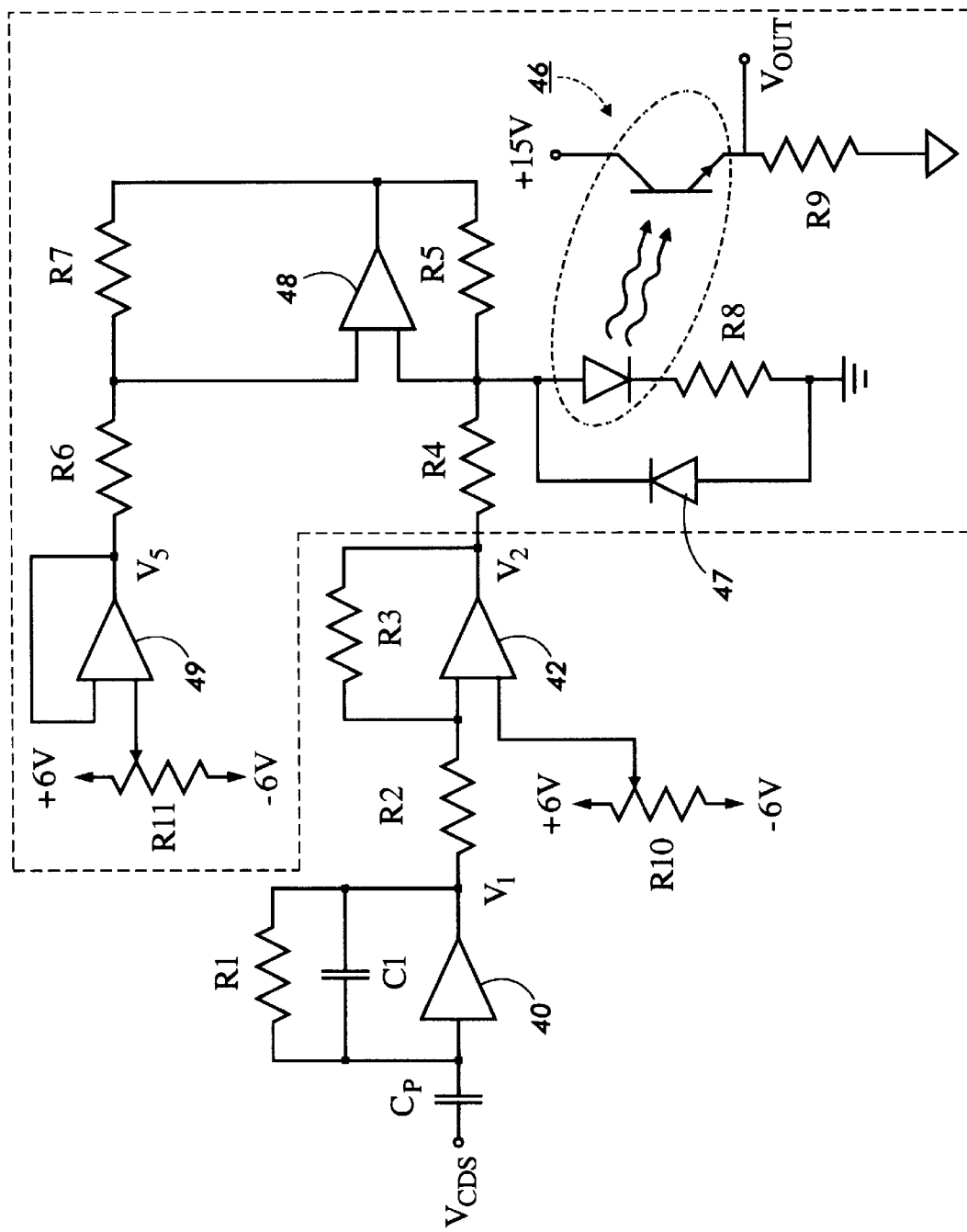
FIG. 3 is a circuit for an optically coupled charge integrating amplifier for the optically coupled scanner system of this invention.

Referring to FIG. 3, an example of a circuit is shown for an optically coupled charge integrating amplifier for the optically coupled scanner system of this invention. The optocoupled part of the amplifier is surrounded by the phantom lines. The first stage of the amplifier integrates the signal $V_{CDS}$ from probe 18 and amplifies it. A charge integrating amplifier 40 such as an Amptek A250 operational amplifier with internal $C_1$=7 pF and $R_1$=300 MΩ feedback components was used as the first stage. A buffer amplifier 42 was used as a second stage to further increase the signal level from integrating amplifier 40. With a gain of 20, amplifier 42 amplified the signal to a level appropriate for the data acquisition board. A variable resistor R 10 in the second stage was used to compensate for unwanted offsets. Compensation for offsets from the first stage integrating amplifier 40 was readjusted each time the gain was changed. If the ground of probe 18 and the amplifier circuit is grounded to zero volts, a serious problem arises. When the outer imaging surface of photoreceptor 12 is at 1000 V and the shield electrode 34 is at 0 V, dielectric breakdown can occur.

Figure 4:
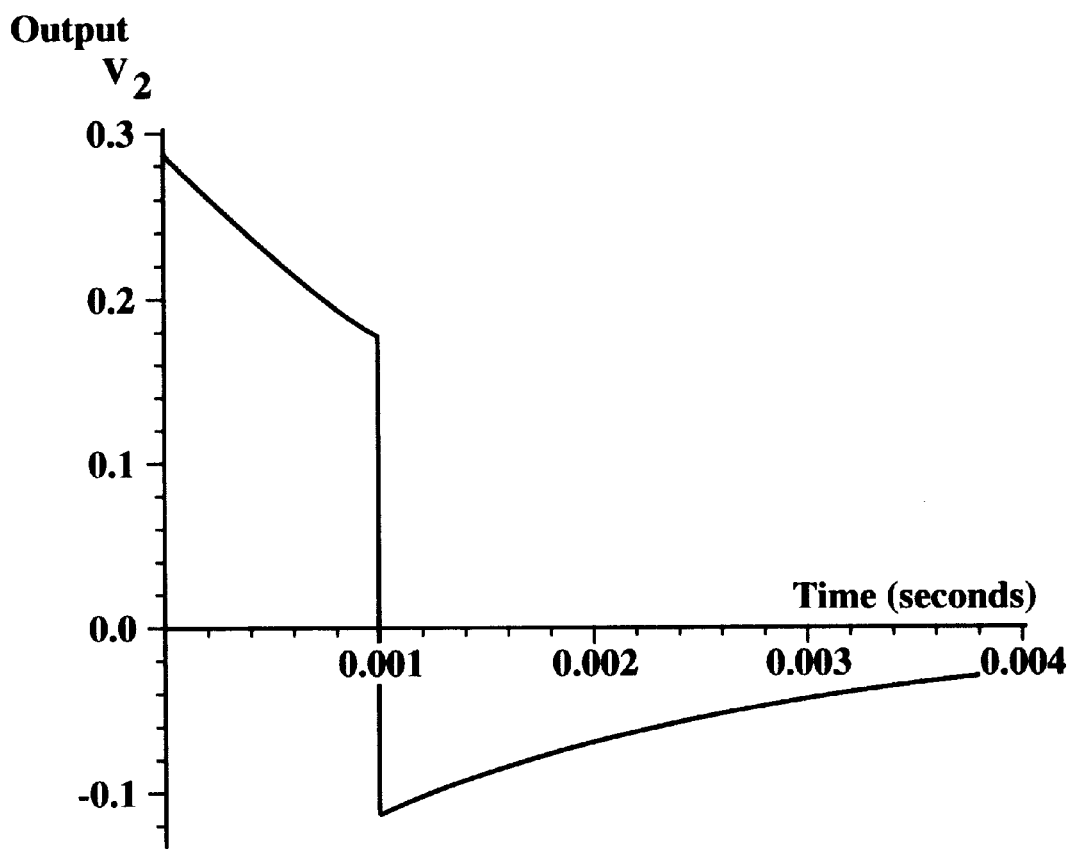
FIG. 4 is a chart illustrating output V2 of the amplifier given in FIG. 3 with 100 volts, 1 ms, square pulse at the input.

Illustrated in FIG. 4 is a chart illustrating output V2 of the amplifier given in FIG. 3 with 100 volts, 1 ms, square pulse at the input illustrating the ac coupling and the time constant of the amplifier.

The capacitance between the probe 18 and ground plane of photoreceptor belt 12 is inversely proportional to the distance between the end 24 of probe 18 and the outer imaging surface of photoreceptor belt 12. To continuously measure a distance, a 100 V square wave pulse was applied to the probe 18 synchronously with the data acquisition frequency, in addition to the bias voltage equal to photoreceptor surface potential. The data acquisition system takes readings at the maximum and minimum points of the 100 V wave. Two consecutive readings by the computer 22 will provide a measurement at 0 and 100 V points of the wave. The distance between these two values is inversely proportional to the local distance between the end 24 of probe 18 and the outer imaging surface of photoreceptor belt 12. Calibration was accomplished with a series of readings. The distance between the end 24 of probe 18 and ground plane of photoreceptor belt 12 incrementally increased by a predetermined fixed amount after each reading. Taking the inverse of these values and fitting them to a straight line produced a slope which is used for calibration. For a given reading difference, the distance can be calculated using the slope. Using these measurements, it has been verified that the probe distance varied by ±25 μm during revolution of drum 12.

Figure 5:
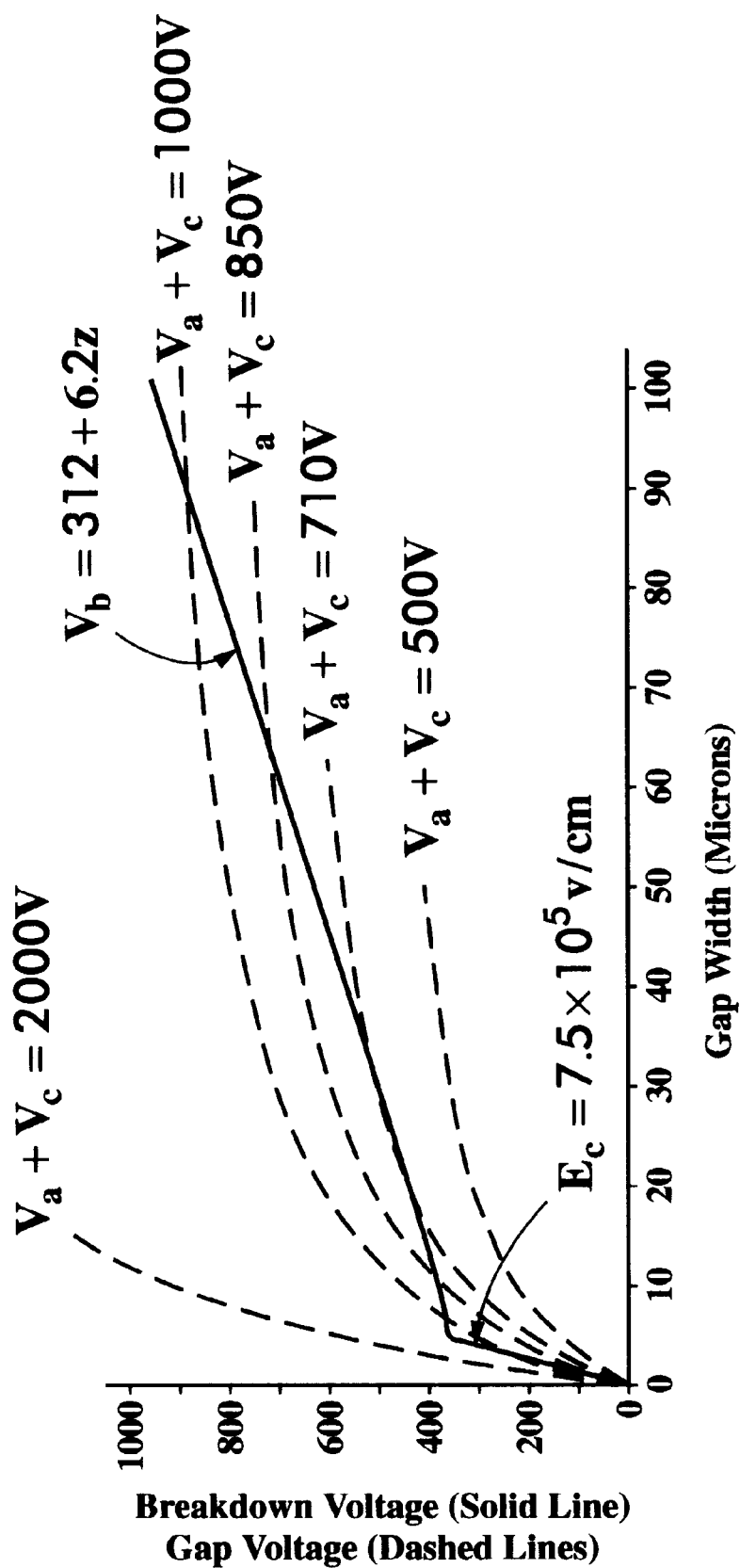
FIG. 5 is another chart illustrating Paschen curves.
Figure 8:
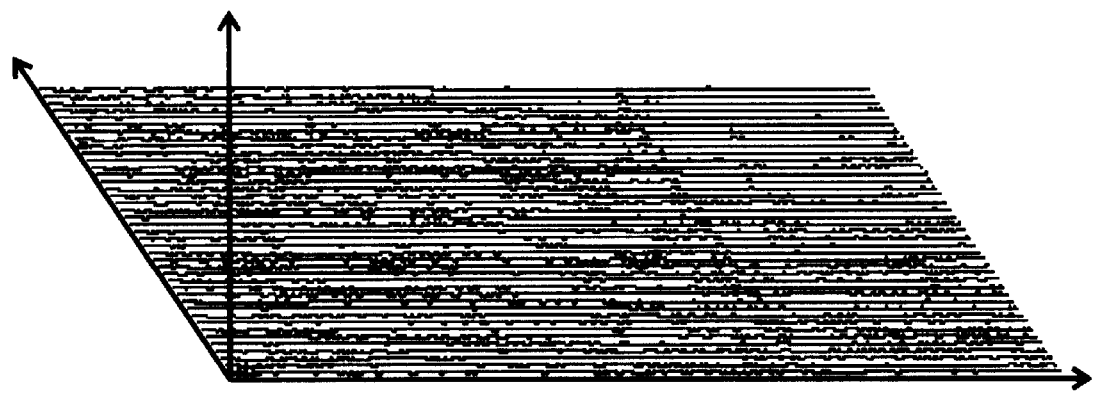
FIGS. 8 through 11 are isometric maps of scanner plots conducted at various charging levels with the optically coupled scanner system of this invention using a 113 micrometer diameter circular center electrode probe.

As shown in FIG. 5, at a 100 μm gap, the Paschen curve can be used to predict when breakdown may occur. Paschen curves are well known in the art and described, for example in R. M. Schaffert, *Electrophotography*, Focal Press Limited, London, 1975. By applying a bias potential to the shield electrode 34 and ground of the probe 18, that is equal to the average potential of the outer imaging surface of the photoreceptor 12, the voltage gradient will be reduced close to zero and prevent breakdown. An electrostatic voltmeter probe 15 e.g. Trek, Model 368 (see FIG. 1), may be used to measure the average surface potential on the outer imaging surface of the photoreceptor 12. The output of voltmeter probe 15 was fed to bias voltage amplifier 20, e.g., Trek 609A (see FIG. 1), which applied the electrical bias to the shield electrode 34 of probe 18. The electrostatic voltmeter probe 15 is a low spatial resolution electrostatic voltmeter which does not sense defects as small as charge deficient spots and thus the bias on shield electrode 34 will not be affected by charge deficient spots. Since arcing can be avoided if the shield electrode 34 is baised to a potential within about ±300 volts of the average surface potential on the outer imaging surface of the photoreceptor 12 and since the average surface potential may be roughly determined by the scorotron grid voltage minus the potential drop due to dark decay, one may alternatively apply a bias on shield electrode 34 without using an electrostatic voltmenter probe 15 so long as the applied bias is within about ±300 volts of the average surface potential on the outer imaging surface of the photoreceptor 12. Thus, for example, when the voltage to the charging scorotron is 1000 volts and the dark decay of the photoreceptor reduces the photoreceptor surface potential to 800 volts, the bias to be applied to the shield electrode of the probe is preferably between about 500 volts and about 1100 volts, i.e. within about ±300 volts of the average surface potential on the outer imaging surface of the photoreceptor. To isolate the computer data acquisition system from the high voltage probe bias, an optoisolator 46 comprising a light emitting diode and a phototransistor has been utilized. The optoisolator 46 is comprised of light emitting diode and a phototransistor in a single package. A Howland voltage to current converter, comprised of the operational amplifier 48 and resistors $R_4$, $R_5$, $R_6$, and $R_7$, powers the light emitting diode of a 4N35 opto-isolator 46 (see components within phantom lines in FIG. 3). Howland voltage to current converters are known and described, for example, in J. I. Smith, Modern *Operational Circuit Design*, John Wiley & Sons, Inc., New York, 1971, the entire disclosure thereof being incorporated herein by reference. Bias current of the voltage to current converter depends on the voltage at $V_5$, and is adjusted using the operational amplifier 49 and the variable resistor ($R_{11}$). The isolated end of the circuit, comprised of phototransistor part of optoisolator 46 and resistor $R_9$ is an emitter follower amplifier which provides the signal of a charge deficient spot without the high voltage component. Optocoupled amplifiers are well known in the electronic art. Any suitable optocoupled amplifier may be employed in the scanning system of this invention. The connecting of the probe to the optocoupled amplifier allows biasing of the probe itself to the photoreceptor average surface potential rather than biasing of the ground plane of the photoreceptor thereby preventing air breakdown and arcing. The optically coupled amplifier denoted by the phantom lines provides the probe signal which is recorded by the data acquisition computer in the scanner system of this invention. The expression "optically coupled" or "optocoupled" as employed herein is defined as providing transmision of an electrical signal without an electrical connection by using an electrically driven light source and a light detector which is insulated from the light source. A key result from using an optically coupled amplifier is that the probe is electrically isolated from the amplifier output and can, therefore, be biased to any potential. Thus, the average surface potential of the surface of photoreceptor 12 is measured with a standard electrostatic voltmeter 15 and the shield electrode 34 of scanner probe 18 is biased to the same potential. In this way the possibility of arcing between the probe end and photoreceptor surface is eliminated and a factor which would greatly impact results of the measurements is overcome. Previously the ground plane of the photoreceptor was biased so that the potential between the probe and photoreceptor surface was zero or very small. This is practical for drums and laboratory experiments but impractical for large belts, in particular for testing rolls of belts in a production environment. The amplifier for probe 15 is an AC coupled amplifier. Therefore only variations of the potential can be measured on the time scale determined by the time constant of the amplifier. This time constant is typically about 2 milliseconds but can be larger or smaller or the amplifier could even be a DC coupled amplifier. In this way only fluctuations in the surface potential are measured with spatial frequency determined by the photoreceptor surface speed and the time constant of the amplifier. With these characteristics the probe 18 is ideally suited to detect charge deficient spots (CDS's) which are very small areas of a photoreceptor having significantly lower potential than the average photoreceptor potential. Charge deficient spots have a potential of more than about 50 volts and occupy an area of between about 20 micrometers and about 200 micrometers. The scanning system of this invention can also be used to detect fluctuations in photoreceptor surface potential induced by any other causes such as coating nonuniformity, nonuniform dark decay, and the like. Thus, the scanner system can serve as an instrument to determine surface potential uniformity on small length scale (less than about 1 millimeter) for which standard electrostatic voltmeter probes are not suitable.

One method of increasing the scanning speed of the photoreceptor surface is to change the shape and the size of probe 18. However, probes having a larger cross sectional area with a large dimension parallel to the direction of scanning lead to loss of resolution compared to probes having a small cross sectional area and a small dimension parallel to in the direction of scanning for the center electrode.

Referring to FIGS. 6 and 7, the use in a probe of a center electrode 59 having a long thin rectangular cross section (the long dimension, i.e. length, being aligned parallel to the axis of the drum 14 similar to a paint brush having a rectangular cross section painting a wide stripe around the periphery of the drum) instead of a circular one will loose resolution only along its width but not along its length which is aligned perpendicular to the direction of scanning. Defects in a photoreceptor which are closely adjacent to each other (aligned along the long dimension, i.e. length, of probe) are perceived as a single large defect in the direction of scanning whereas individual defects in adjacent scan paths (each path being different and parallel to each other) are still perceived individually. The fabrication of a rectangular probe 60 containing a rectangular center electrode 59, is slightly more involved than that of an embedded wire probe having a circular cross section. For example, a small piece of shim stock, a 200 μm thick (width of cross section), 5 mm long (length of cross section) bronze plate, may be used as the center electrode 59. Center electrode 59 is supported by a shield electrode 62 which comprises a machined or molded metal structure 64 on one side and flange 66 on the other side. Any suitable fasteners, such as allen screws 68, tightly sandwich center electrode 59 between machined metal structure 64 and flange 66. On both sides of center electrode 59, an electrical insulating material such as 0.001" thick Teflon 69 is added to insulate center electrode 59 from shield electrode 62. The edges of center electrode 59 are rounded to prevent sharp edges from piercing through the insulating material and shorting the probe. A downwardly extending extension 70 from long rectangular probe 60 having a suitable smaller width than the main probe 60, such as a width of 10 millimeters, is preferred to facilitate easier alignment of probe 60 with the outer imaging surface a photoreceptor. The probe 60 is polished to ensure that the bottom of extension 70 is parallel with the outer surface of the photoreceptor. Thus, as illustrated in FIGS. 6 and 7, center (sensing) electrode 59 is completely shielded on all sides by shields 64 and 66.

Figure 9:
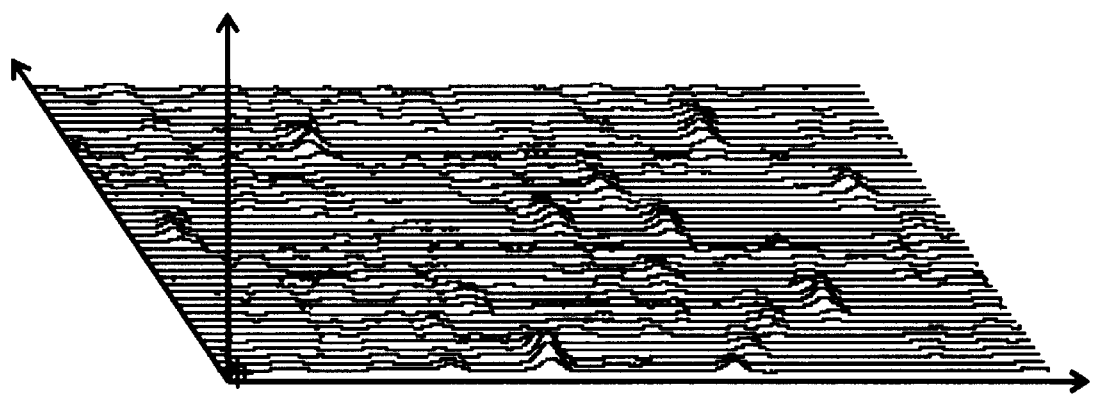
Figure 10:
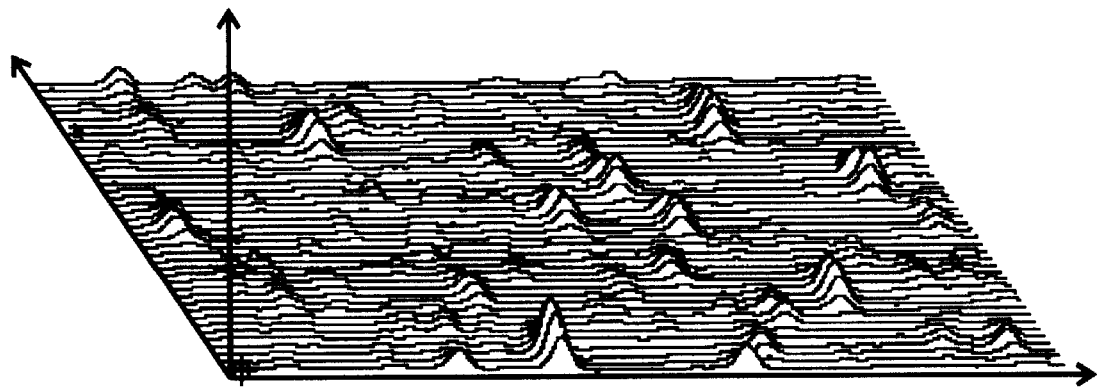
Figure 11:
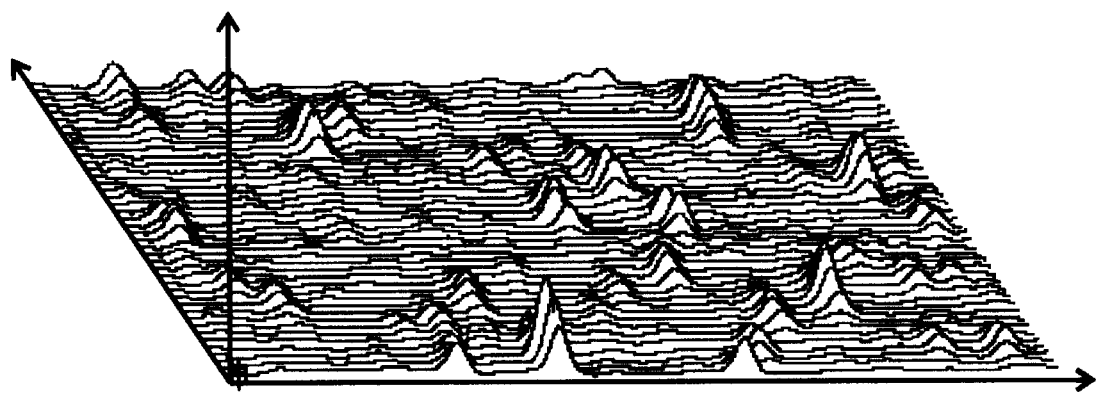

Using a probe with a center electrode having a circular cross section of 113 micrometers, a number of scans of the same area of a photoreceptor were performed with different charging levels with a system similar to that illustrated in FIG. 1. The results, recorded using a computer and reproduced by an ink-jet printer, are illustrated in FIGS. 8 through 11. The first scan, shown in FIG. 8, was conducted with an uncharged photoreceptor and indicates the level of noise present in the system. No structure is present because no defects are present without charging. As the voltage is increased, defect structures appear as shown in FIGS. 9, 10 and 11 at 500 volts, 800 volts and 1000 volts of charging, respectively. Similar structure is present in all of the scans with the exception of the first. This demonstrates that the measurement results are reproducible. In fact, two successive scans with the same charging voltage were found to give indistinguishable results. The "height" of the defects increases with increasing charging voltage.

Employing a probe with a center electrode having a rectangular cross section, a number of scans of the same area of a photoreceptor were performed with different charging levels with a system similar to that illustrated in FIG. 1 and probe similar to that shown in FIGS. 6 and 7. The data from the rectangular probe lacked the structure achieved with the probe having a circular cross section which was expected as the structure was averaged by the larger area probe.

Figure 12:
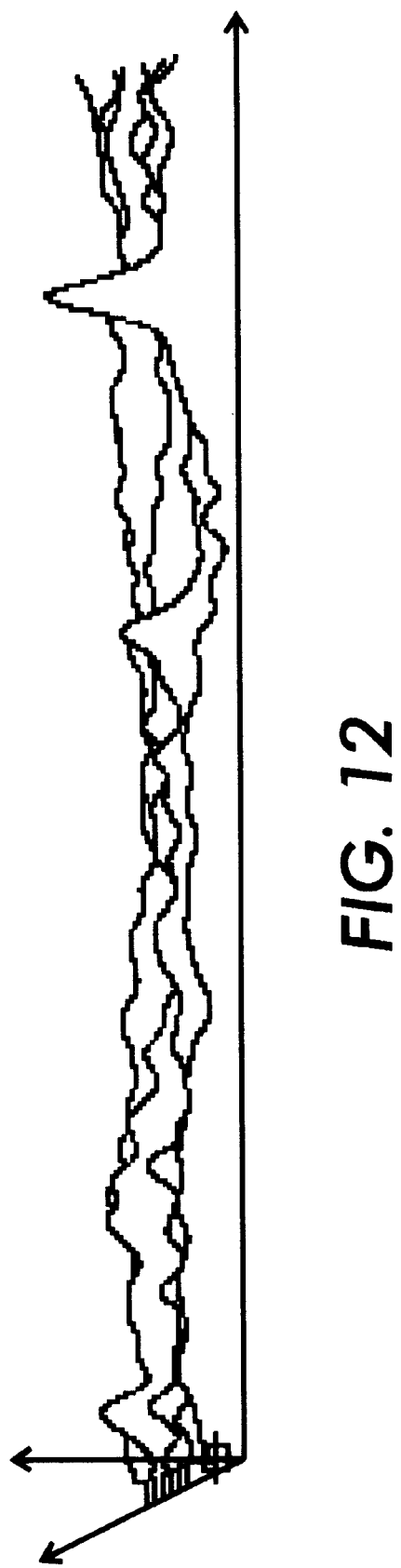
FIG. 12 is a scan plot approximating a 5 mm probe using data from a 113 micrometer diameter circular center electrode probe.
Figure 13:
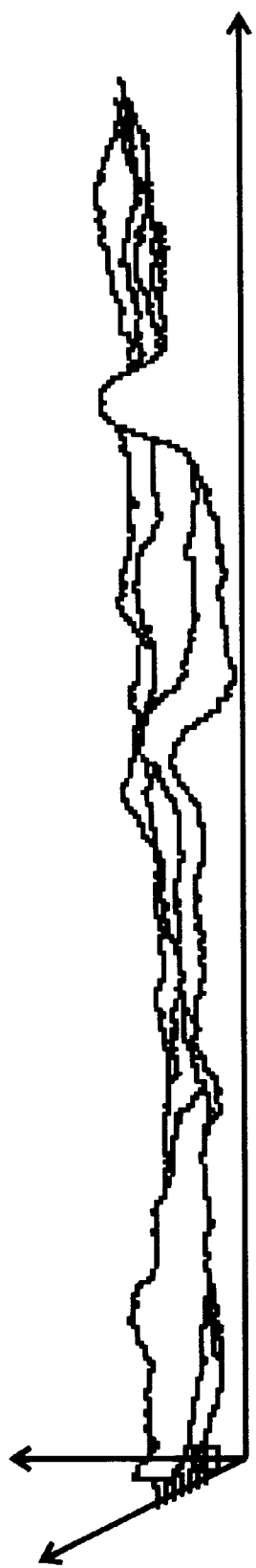
FIG. 13 is a scan plot performed with a 5 mm long 200 micrometer thick rectangular probe.

A scan performed using a probe having a 113 μm diameter circular center electrode was processed through the convolution computer program to approximate the results achievable with a center electrode having a rectangular cross section that is 200 μm wide and 5 mm long is shown in FIG. 12. The long side of the rectangular electrode was aligned parallel to the axis of the drum and perpendicular to the scanning path. The slowly varying curves illustrated in FIG. 13 (scan actually made with the 200 μm wide and 5 mm long center electrode having a rectangular cross section) do not all correspond to the predicted values in FIG. 12, but most of the peaks of the FIGS. do correspond to each other.

Generally, a probe with center electrode having a round cross section provides higher resolution than a probe with center electrode with a rectangular cross section, the linear dimension of both electrodes being the same in the scanning direction. For center electrodes having a round or circular cross section, satisfactory results may be achieved with a diameter between about 20 micrometers and about 500 micrometers. Preferably, the diameter is between about 100 micrometers and 200 micrometers. When the diameter is less than about 20 micrometers, the signal from the probe may be too small to be accurately detected. If the diameter is greater than about 500 micrometers, the probe resolution becomes similar the spatial resolution of standard electrostatic voltmeter probes. For center electrodes having a rectangular cross section, satisfactory results may be achieved with a width between about 20 micrometers and about 500 micrometers and a length of between about 0.5 millimeter and about 10 millimeters, the length (longest side) being the side of the electrode which is perpendicular to the direction of scan (e.g. the direction of scan in the embodiment shown in FIG. 1 is in a direction perpendicular to the axis of drum 14 and parallel to an imaginary line circumscribing the drum). When the width is less than about 20 micrometers, probe sensitivity decreases significantly. If the width is greater than about 500 micrometers, conventional electrostatic voltmeter probes become more suitable for these measurements. When the length is less than about 0.5 millimeter, there is relatively small increase in the scanning speed of the photoreceptor area. If the length is greater than about 10 millimeters, the probe noise may become a problem.

For a circular 100 μm diameter probe, photoreceptor drum diameter of 3" (7.62 cm) and rotation speed of 1 revolution per second, a scanned speed of 1 in$^2$/min (6.45 cm$^2$/min) has been achieved with scanning system of this invention. In order to achieve this speed, the data acquisition rate is about 2.5 kHz which is easily accessible by conventional digital data acquisition instrumentation available for any suitable personal computer. For a rectangular 0.2 millimeter×5 millimeter probe center electrode, where the 5 millimeter side was parallel to the axis of the photoreceptor drum, a scanning speed of 13 in$^2$/min (83.85 cm$^2$/min) was achieved. The scanning speeds in experiments conducted were limited by computer speed and time necessary to move the probe parallel to the drum axes. These speeds can be further increased by using probe arrays and faster computers for data processing. This enables on-line inspection for charge deficient spots as photoreceptors are being coated. Scanning speeds can be at least about 1 inch per second and include, for example, scanning of the imaging surface with the probe at a speed of between about 1 inch per second and about 100 inches per second.

Figure 14:
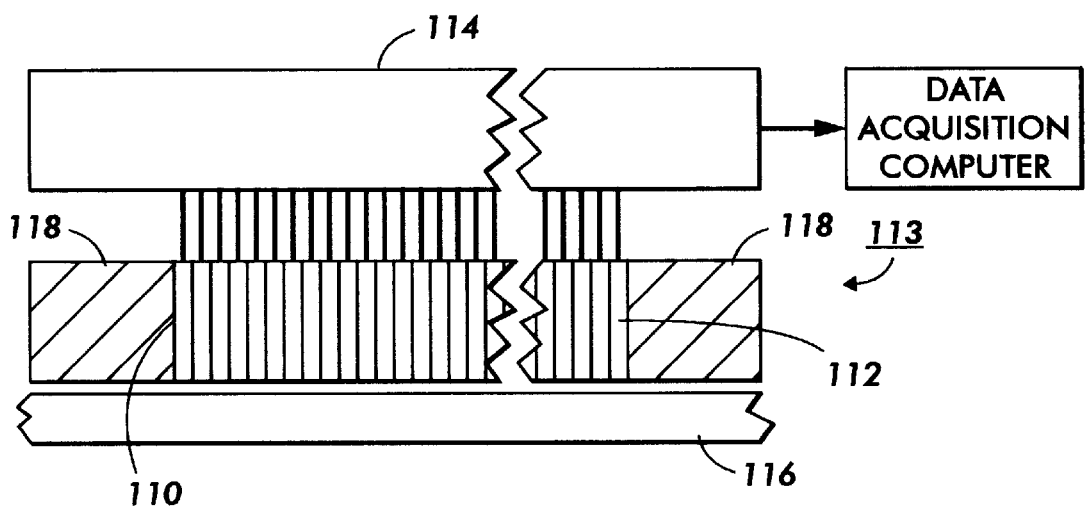
FIG. 14 is an array of probe elements ganged together.

As shown in FIG. 14, multiple scanner probes including first probe electrode element 110 through Nth probe electrode element 112 may be ganged together into an array 113 and operated in a multiplex mode with an N channel optically coupled amplifier 114 outputting to a data acquisition computer. This type of system will increase the rate of scan of the surface of an electrostatographic member 116. Each probe electrode element is electrically insulated from the surrounding shield 118.

Figure 15:
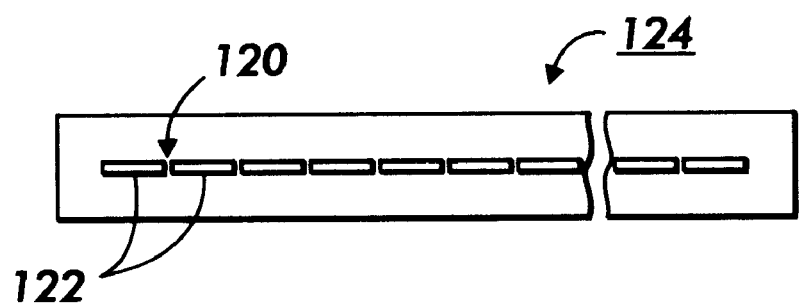
FIG. 15 is an array of probe elements ganged together with small gaps between elements illustrated.
Figure 16:
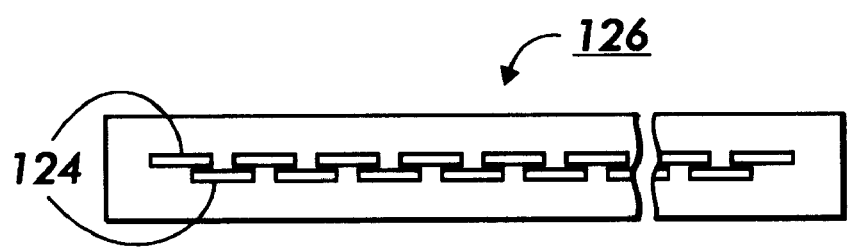
FIG. 16 is an array of probe elements ganged together in staggered rows.

As illustrated in FIG. 15, small gaps 120 may be provided between different electrode elements 122 of a probe array 124. Preferably, but not necessarily, the gap may be smaller than the gap distance between the end of probe array 122 and the adjacent surface of an electrostatographic member. While the probe electrode elements 122 in FIG. 15 are shown aligned in a single row, they may be arranged as staggered probe electrode elements 124 in the array 126 illustrated in FIG. 16. The staggered probe electrode arrangement enables the scanning of the photoreceptor surface without any effects normally encountered due to small gaps between individual probe elements of a single row array.

The contactless scanner system of this invention detects charge deficient spots in electrostatographic members such as xerographic photoreceptors at a high speed. Thus, for example, the very high speed of scans achieved with the scanning system of this invention compared to present state of the art techniques, such as the stylus scanner, result in an improvement by a factor of more than 100. Large area scans, e.g. of a one pitch photoreceptor is feasible in a reasonable time vs. 1 cm$^2$ with a stylus scanner. The results provided by the high speed scanner system of this invention are highly reproducible and the number of point like defects increase in magnitude and number as the charging level is increased. Charge associated with charge deficient spots for a photoreceptor can be detected with the system of this invention, taking into account probe distance variations. This number correlates well with photoreceptor gradings. Statistical measures produced by the contactless scanner system of this invention also indicate photoreceptor quality. Values for the higher order moments of the potential fluctuations on the photoreceptor surface indicate the number and magnitude of charge deficient spots. A poor quality photoreceptor has large higher moments. Higher order moments are a well known statistical tool.

Electrophotographic (e.g. photoreceptor) flexible belt and rigid drum imaging members are well known in the art. They may comprise one or more electrically operative layers usually supported on a substrate. Typical examples of photosensitive members having at least two electrically operative layers including a charge generator layer and charge transport layer are disclosed in U.S. Pat. Nos. 4,265,990, 4,233,384, 4,306,008, 4,299,897 and 4,439,507. The disclosures of these patents are incorporated herein in their entirety.

The innovative non-contacting scanner system of this invention includes an optocoupled high resolution probe which can be capacitatively coupled with the surface of an electrostatographic member. Optical coupling of a charge integrator of the high resolution probe to the external circuit allows the probe to be biased close to the potential of the photoreceptor surface and eliminates the possibility of breakdown of air. The photoreceptor surface potential is measured by an electrostatic voltmeter which feeds the signal to a bias voltage amplifier to control biasing of the high resolution probe. The assessment system of this invention is rapid and does not require fabrication of belts and extensive testing in print engines, nor extensive scanner testing, nor numerous reports from repairmen in the field. The testing system of this invention is very rapid with an improvement factor of more than 100 over stylus scanners. Moreover, the assessment preformed with the process of this invention is more accurate and free of dilution by unrelated effects due to machine interactions occurring in machine testing. Also, on line measurements and screening of production electrostatographic webs may be accomplished with the scanning system of this invention. Different configurations of electrostatographic imaging members such as belt and drum photoreceptors may also be evaluated with the scanning system of this invention.

The scanning system of this invention may also be utilized to scan and digitize electrostatic latent images carried by imaging members. The electrostatic latent images may be formed on the imaging members by any suitable technique. Typical techniques for forming electrostatic latent images include, for example, electrophotographic processes and electrographic methods. In electrophotographic processes, a photoconductive imaging member is uniformly charged in the dark and thereafter exposed to activating radiation in image configuration thereby selectively discharging the photoreceptor to form the electrostatic latent image. The photoconductive imaging member may be of any suitable type comprising photoconductive material that is sensitive to activating radiation such as infrared radiation, visible light, X-rays, ultraviolet radiation, and the like. Electrographic latent images are formed on dielectric imaging members using suitable imagewise charging devices such as shaped electrodes, styli, stencils, ion streams and the like. The electrostatic latent image (e.g., comprising a pattern of charged areas and areas having little or no charge) is scanned and converted to digital signals by the scanning system of this invention. The digitized signals representative of the electrostatic latent image may be stored and subsequently used for any suitable purpose such as producing a hard copy for diagnostic purposes in case of X-ray imaging, processing with pattern recognition software, detection of image defects, electronic manipulation, and the like.

PREFERRED EMBODIMENT OF THE INVENTION

A number of examples are set forth hereinbelow and are illustrative of different compositions and conditions that can be utilized in practicing the invention. All proportions are by weight unless otherwise indicated. It will be apparent, however, that the invention can be practiced with many types of compositions and can have many different uses in accordance with the disclosure above and as pointed out hereinafter.

EXAMPLE I

Figure 17:
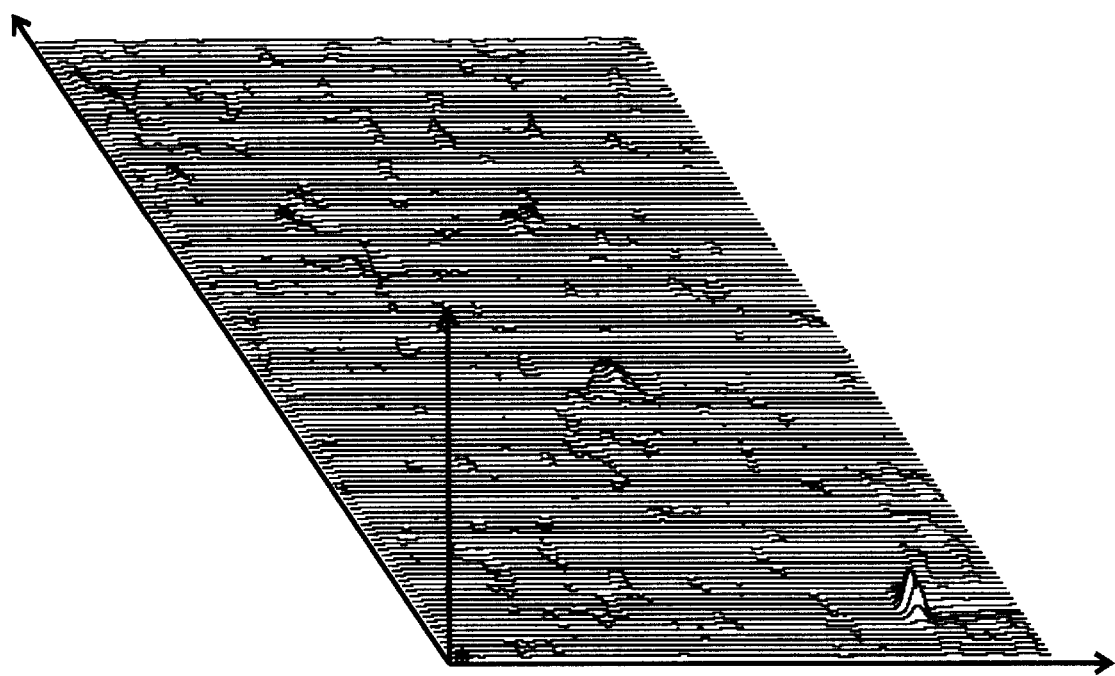
FIGS. 17 and 18 are isometric maps of scanner plots of two different photoreceptors, with small and large number of CDS's, respectively, conducted with the optically coupled scanner system of this invention, using a 113 micrometer diameter circular center electrode probe.
Figure 18:
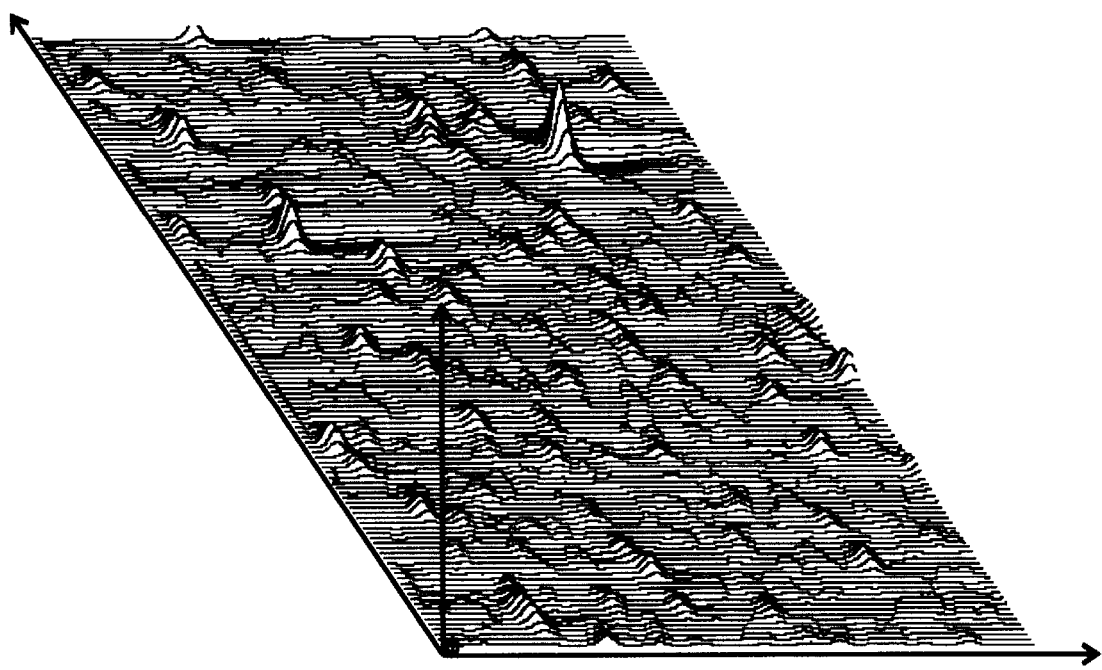

Two conventional belt photoreceptors were prepared at different times using the same conventional coating fabrication techniques. Rectangular 3 inch×15 inch (7.62 cm×38.1 cm) pieces of the photoreceptor belt were cut and mounted on the drum schematically presented in FIG. 1. FIGS. 17 and 18 show the printed output of optically coupled scanner runs from the two belt photoreceptors. The optical coupled scanner circuitry is described in detail with reference to FIG. 3. The scanner output was printed using a conventional inkjet printer. The sample used for FIG. 17 had a relatively low number of charge deficient spots and was classified as a Type I sample. The one used in FIG. 18 had a very large number of charge deficient spots and was classified as a Type IV sample. This classification was based on print tests made with a xerographic copier. Both the Type I and Type IV photoreceptors were scanned at a rate of 1 in$^2$/min (6.45 cm$^2$/min) with a probe containing a center electrode with a circular cross section having a diameter of 113 μm. The difference between the two samples can easily be seen in the scan results shown in FIGS. 17 and 18. Each belt was scanned again several times. Each time, the same map was reproduced indicating that the defects were not artifacts but ingrained in the photoreceptors. The scanner provides an ultra accurate scan of photoreceptors and clearly distinguishes between photoreceptors with low and high number of charge deficient spots. The second moment of the surface potential fluctuations around a mean surface potential was 47 (relative units) for Type I photoreceptor and 408 (relative units) for Type IV photoreceptor, which represents a significant difference.

EXAMPLE II

Figure 19:
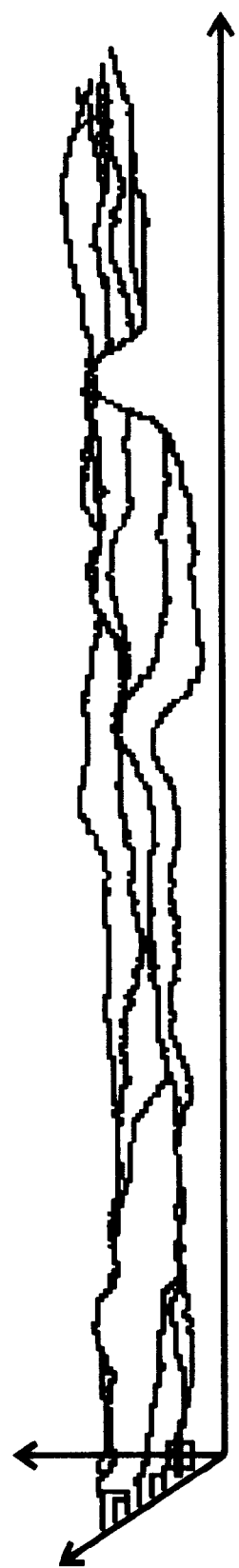
FIG. 19 is a scan plot using a rectangular electrode probe of a photoreceptor with a small number of charge deficient spots.
Figure 20:
FIG. 20 is a scan plot using a rectangular electrode probe of a photoreceptor with a large number of charge deficient spots.

Measurements were made on the same two photoreceptors from Example I using a probe with a rectangular electrode 0.2 mm wide and 5 mm long. The scanning speed was 13 in$^2$/min (83.85 cm$^2$/min). The plots for the Type I and Type IV photoreceptors are shown in FIGS. 19 and 20, respectively. The photoreceptor with a small number of charge deficient spots (Type I) and a large number of charge deficient spots (Type IV) are clearly distinguishable from FIGS. 19 and 20. It is immediately obvious that the structure provided by these rectangular probe scans is not as revealing as in the 113 μm diameter probe scans. There is also variation of the baseline of the data for rectangular probe scans, but the difference in Type I and Type IV photoreceptor scans is nevertheless apparent. Each sample was scanned again several times. Each time, the peaks in the scans are reproduced suggesting that the defects seen are not artifacts but ingrained in the photoreceptor samples.

Thus, both the circular and rectangular probes provide higher scan speeds than prior scanning systems such as a scanning stylus. Also, the circular center electrode probe provides higher resolution than the rectangular center electrode probe whereas the rectangular center probe covers a large area per unit time than the circular center electrode probe. Further, the scanning systems of this invention provide a means for rapidly assessing freshly fabricated substandard photoreceptors.

Although the invention has been described with reference to specific preferred embodiments, it is not intended to be limited thereto, rather those having ordinary skill in the art will recognize that variations and modifications may be made therein which are within the spirit of the invention and within the scope of the claims.

What is claimed is:

1. A contactless process for detecting surface potential charge patterns in an electrophotographic imaging member comprising
   providing an electrophotographic imaging member comprising at least one photoconductive imaging layer having a first major surface on one side and a second major surface on the opposite side, said second major surface comprising an imaging surface,
   providing a scanner comprising a capacitive probe having an outer shield electrode,
   maintaining said probe adjacent to and spaced from said imaging surface to form a parallel plate capacitor with a gas between said probe and said imaging surface,
   providing a probe amplifier coupled to said probe, said probe amplifier having an optically coupled output,
   establishing relative movement between said probe and said imaging surface,
   maintaining a substantially constant distance between said probe and said imaging surface,
   applying a constant voltage charge to said imaging surface prior to relative movement of said probe and said imaging surface past each other,
   synchronously biasing said probe to within about ±300 volts of the average surface potential of said imaging surface, and
   measuring variations in surface potential with said probe.

2. A contactless process according to claim 1 wherein said capacitive probe comprises an inner electrode surrounded by and insulated from an coaxial outer shield electrode.

3. A contactless process according to claim 2 wherein said inner electrode has a circular cross section.

4. A contactless process according to claim 3 wherein said circular cross section has a diameter between about 20 micrometers and about 500 micrometers.

5. A contactless process according to claim 2 wherein said inner electrode has a rectangular cross section.

6. A contactless process according to claim 5 wherein said cross section has a width between about 20 micrometers and about 500 micrometers and a length between about 0.5 millimeter and about 10 millimeters.

7. A contactless process according to claim 1 wherein said probe has an end facing said imaging surface, said end having a surface which is parallel to said imaging surface.

8. A contactless process according to claim 1 wherein said constant distance between said probe and said imaging surface is between about 20 micrometers and about 200 micrometers.

9. A contactless process according to claim 1 wherein said probe amplifier optically coupled to said probe is an AC coupled amplifier.

10. A contactless process according to claim 1 including measuring variations of said potential on a time scale determined by time constant of said amplifier.

11. A contactless process according to claim 1 wherein said probe amplifier optocoupled to said probe is a DC coupled amplifier.

12. A contactless process according to claim 1 including measuring variations of said potential with spatial frequency determined by imaging surface speed and time constant of said amplifier.

13. A contactless process according to claim 1 wherein said charge patterns in said electrophotographic imaging member are charge deficient spots having a potential of more than about 50 volts, said charge deficient spots occupying an area of between about 20 micrometers and about 200 micrometers.

14. A contactless process according to claim 1 wherein said charge patterns in said electrophotographic imaging member are fluctuations in potential in said imaging surface potential induced by variations in coating thickness.

15. A contactless process according to claim 1 wherein said charge patterns in said electrophotographic imaging member are fluctuations in potential in said imaging surface potential induced by variations in dark decay.

16. A contactless process according to claim 1 wherein said charge patterns in said electrophotographic imaging member are fluctuations in potential in said imaging surface potential induced by coating defects.

17. A contactless process according to claim 1 wherein said charge patterns in said electrophotographic imaging member are fluctuations in potential in said imaging surface potential induced by fluctuations in sensitivity in the charge generator layer.

18. A contactless process according to claim 1 wherein said charge patterns in said electrophotographic imaging member are measured on a length scale of less than about 1 millimeter.

19. A contactless process according to claim 1 wherein said imaging member is a drum.

20. A contactless process according to claim 1 wherein said imaging member is a flexible belt.

21. A contactless process according to claim 1 including scanning said imaging surface with said probe at a speed of at least about 1 inch per second.

22. A contactless process according to claim 1 including scanning said imaging surface with said probe at a speed of between about 1 inch per second and about 100 inches per second.

23. A contactless process according to claim 1 wherein said imaging member is a flexible web supported on a rotatable drum.

24. A contactless process according to claim 1 including measuring said average surface potential of said imaging surface with a low spatial resolution electrostatic voltmeter.

25. A contactless process according to claim 24 including compensating said surface potential variations for variations in distance between said probe and said imaging surface and comparing the compensated voltage values to a baseline voltage value to detect charge patterns in said electrophotographic imaging member.

26. A contactless scanning system comprising a high resolution capacitive probe, a low spatial resolution electrostatic voltmeter coupled to a bias voltage amplifier, and an electrophotographic imaging member having an imaging surface capacitively coupled to and spaced from the probe and the voltmeter, the probe comprising an inner electrode surrounded by and insulated from a coaxial outer Faraday shield electrode, the inner electrode coupled to a probe amplifier, the probe amplifier having an optically coupled output, and the Faraday shield connected to the bias voltage amplifier.

27. A contactless scanning system according to claim 26 wherein said system comprises a plurality of said probes ganged together for operation in a multiplex mode.

* * * * *